United States Patent [19]

Ducheyne et al.

[11] Patent Number: 5,120,340
[45] Date of Patent: Jun. 9, 1992

[54] BIOREACTIVE MATERIAL FOR A PROSTHESIS OR COMPOSITE IMPLANTS

[75] Inventors: Paul Ducheyne, Byrn Nawr, Pa.; Louis Van Hove, Mol, Belgium; Evert Schepers, Leuven, Belgium; Raymond Kempenners, Mol, Belgium; Marcel DeClercq, deceased, late of Rotsellar, Belgium, by Maria M. Van Hoeylandt, legal representative

[73] Assignee: S.A. FBFC International, Brussels, Belgium

[21] Appl. No.: 704,202

[22] Filed: May 22, 1991

Related U.S. Application Data

[62] Division of Ser. No. 578,276, Sep. 6, 1990.

[30] Foreign Application Priority Data

Sep. 6, 1989 [FR] France ............... 89 11857

[51] Int. Cl.$^5$ .............. C03B 1/00; C03B 11/14; C03C 3/078
[52] U.S. Cl. ............... 65/18.3; 65/33; 65/59.5; 65/18.1; 623/16; 501/3; 501/10; 106/35; 264/60; 264/16
[58] Field of Search ............ 501/10, 3; 106/35; 65/18.1, 33, 18.4, DIG. 15, 59.5, 30.1, 18.3; 264/60, 16, 17; 623/16, 16 A–16 G

[56] References Cited

U.S. PATENT DOCUMENTS

| | | | |
|---|---|---|---|
| 3,669,715 | 6/1972 | Meyer | 264/60 |
| 3,929,971 | 12/1975 | Roy | 423/308 |
| 3,981,736 | 9/1976 | Broemer | 501/10 |
| 4,120,730 | 10/1978 | Trojer | 501/3 |
| 4,560,666 | 12/1985 | Yoshida | 501/5 |
| 4,772,436 | 9/1988 | Tyszblat | 65/33 |
| 4,775,646 | 10/1988 | Hench | 501/2 |
| 4,851,046 | 7/1989 | Low | 106/35 |
| 4,917,702 | 4/1990 | Scheicher | 501/151 |
| 5,074,916 | 12/1991 | Hench | 623/16 |

FOREIGN PATENT DOCUMENTS

9008520 8/1990 World Int. Prop. O. ........... 623/16

OTHER PUBLICATIONS

Kingery W., Introduction to Ceramics, 1976, 2nd ed, p. 501.
Tooley, F. V., The Handbook of Glass Manufacture, 3rd ed, 1984, pp. 28–29.

*Primary Examiner*—W. Gary Jones
*Assistant Examiner*—John Hoffman
*Attorney, Agent, or Firm*—Dennison, Meserole, Pollack & Scheiner

[57] ABSTRACT

A method is disclosed for preparing an improved bioreactive material of the glass or partially crystallized glass type for bone prostheses or dental implants, which can be welded to bone tissue by chemical bonding. The material consisting essentially of, by weight, 5 to 14% $Na_2O$, 0 to 12% $P_2O_5$, 49 to 57% $SiO_2$, and balance, no more than 33% $CaO + CaF_2$, the material containing 0.5 to 7% $CaF_2$, and is prepared by a method comprising the steps of preparing a mixture of powders constituting a precursor of the material made of carbonates, phosphates, silica, oxides and fluorides, melting, homogenizing, casting and cooling the mixture to obtain an intermediate, non-crystallized glass, optionally annealing, and then grinding, either pressing the non-crystallized ground glass obtained cold to shape it, then sintering naturally or under a load after degassing, or sintering under a load directly after degassing, then cooling and optionally polishing or machining.

16 Claims, No Drawings

BIOREACTIVE MATERIAL FOR A PROSTHESIS OR COMPOSITE IMPLANTS

This is a divisional of copending application Ser. No. 07/578,276, filed Sep. 6, 1990.

FIELD OF THE INVENTION

The invention conerns a bioreactive material of the glass type and a method of manufacturing it. The material is generally designed to be implanted, in composite form, joined to a structural material generally with a low coefficient of expansion, in a human or animal body, for example as a dental implant or a bone prosthesis.

DESCRIPTION OF RELATED ART

Bone prostheses and implants are made from materials such as metals, ceramics, polymers and composites. They can be differentiated by their reactivity with the skeleton. Apart from excellent biocompatibility they need to have very good mechanical properties and, in the case of dental implants, must allow for mastication.

The bonds and/or attachments to the bone tissue may be formed in various ways: mechanical attachment, sticking with organic or inorganic cement, or biological anchoring. In the last case the bond may be formed either by a porous layer provided on the prosthesis, so that the regrowing bone invades and fills the pores, or with a chemical bond between a prosthesis of bioreactive material and the bone tissue (biological anchoring by osteoconductivity).

This invention is concerned with prostheses or implants of bioreactive material (based on glass or ceramics) which gives rise to biological anchoring through chemical bonding with the bone. Prostheses or implants, like anchoring means, must withstand strong mechanical stresses, particularly resistance to fracture. The invention therefore relates more particularly to prostheses or implants made from said materials, reinforced by fibres or other substrates (structural material) with good mechanical properties. In particular one can thus make dental implants comprising two parts: a root implanted in the bone of the jaw, on which a permucosal passage will then be fixed to receive the external dental prostheses.

Materials based on hydroxyapatite $Ca_{10}(PO_4)_6(OH)_2$, tricalcium phosphate $Ca_3(PO_4)_2$ in its alpha or beta forms, or preferably bioglasses have great bioactivity. Bonds obtained between them and bone lead to a change in the composition of the surface reaction layer, located on said material at the interface with the bone. Animal experiments have shown that the surface reaction layer lacks mechanical strength under load, because the reaction migrates to the interior of the material. To avoid this lack of strength, Applicants have sought to reduce the thickness of the reaction layer while maintaining its capacity to bond with the bone tissue; they have thus sought to develop materials (reinforced on non-reinforced glasses and ceramics) with reduced bioreactivity.

The bioactive materials may be used to make composite prostheses or implants containing reinforcing structural material, comprising e.g. a metal or a ceramic and consequently having improved mechanical properties. The composites made may be plated or reinforced.

Prostheses or implants made of bioglass and reinforced with stainless steel fibre, in which the bioglass and stainless steel adhere well to one another, have been tried out on animals. But stainless steel reinforced implants have disadvantages. In particular, the steel has to be sheathed in glass, but after a certain implantation time the sheath is found to have cracked. The steel thus exposed comes into contact with the biological medium and unacceptable inflammatory reactions take place around those points. These reactions interfere with osteogenesis, prevent good bonding with bone tissue and thus limit the strength of the connection. Exposure also takes place when there are defects (e.g. cracks) at the periphery of the bioglass sheath. To avoid such exposure of the steel, machining of prostheses or implants is prohibited in particular. The inflammation may be though to be due to the joint action of emission of stainless steel ions and glass ions. Furthermore the use of stainless steel should be avoided because of its poor biocompatibility.

Thus Applicants have sought to make bioglass composites reinforced by structural materials which have good biocompatibility, like some metals such as Ti or Nb or Ta, or like ceramics. Such structural materials can thus be bared and exposed to the biological medium without any disadvantages connected with biocompatibility. Furthermore adhesion between the bioreactive material and the structural material must be as strong as possible. On this subject Applicants have found that hydroxyapatites, tricalcium phosphates or bioglasses as normally used in prior art still have imperfect adhesion to the structural materials envisaged by them. Poor adhesion may in fact cause the reinforcing material to be freed, e.g. when masticating force is applied; in particular it gives the metal reinforced composite obtained inadequate mechanical properties.

Furthermore Applicants have sought to perfect not only improved main chemical bonding between the glass and the bone tissue but also a secondary mechanical gripping effect, as a result of the bone tissue growing into the rough parts or undulations created by surface dissolution of the bioreactive material, which tends to improve the mechanical strength of the implantation. These rough parts or undulations generally form in a composite of reinforced bioactive material, where the structural material shows at the surface after partial dissolution of the bioreactive material.

Thus U.S. Pat. No. 4,478,904 (DUCHEYNE) describes a reinforced composite comprising a skeleton of stainless steel fibre which is impregnated by dipping it into the molten bioglass then solidified. A composite of this type has the disadvantage of using stainless steel, which has poor biocompatibility, retards osteogenesis and leads to the above-mentioned disadvantages.

Particularly in the case of this combination of stainless steel and bioglass, it will noted that an intermediate layer forms between the composite and the ossified tissue formed. The intermediate layer is relatively thick (about 200 to 300 microns), relatively weak and breaks when the implant is mechanically stressed. Small cracks may then appear in the bioglass, so that bubbles of non-bone tissue form in those places and interfere with the regeneration of bone tissue. With this type of excessively bioreactive glass therefore, biological anchoring is insufficiently strong and the biological reaction is not limited to a surface reaction layer; instead it spreads inside the glass material, leading to its embrittlement. In addition, the type of glass described has insufficient adhesion to the reinforcing materials envisaged by Applicants.

Application EP 0 206 726 (Florida) describes the same type of glass formulation with great bioreactivity, for the purpose of obtaining granulates which can help to repair cavities or defects in bones.

U.S. Pat. No. 4,775,646 (HENCH) describes two bioreactive glasses of a composition which comes within the ranges of glasses described in the two previous documents, but where part (30 to 60 molar percent) of the lime is replaced by $CaF_2$. The purpose is to reduce the reactivity of the glass obtained, in order to increase its resistance to demineralisation in a biological medium. Thus the glasses contain at least 10% by weight of $CaF_2$; such a quantity of fluoride may present toxicity dangers. It will also be noted that after fusion and solidification the glasses contain crystallised species (apatites and the like) (FIGS. 2, 6, etc.).

The Journal of Materials Science (JMS) Vol. 23 (1988) pages 4295-4299, describes a glass composition which, after fusion and solidification, contains crystalline phases with improved mechanical properties. It does not contain any fluoride.

SUMMARY OF THE INVENTION

Faced with these problems, Applicants have sought firstly to perfect a bioreactive material which, when combined with a reinforcing (or structural) material, will give composite pieces with improved biocompatibility. The reinforcing materials envisaged particularly include titanium, but also niobium and tantalum, or ceramics such as carbides, nitrides or borides, in the form of powder, fibres, whiskers, a porous skeleton etc.; these in themselves already have good biocompatibility.

They have also attempted to obtain a bioreactive material of the glass type, or preferably the partially or totally crystallised glass type, which would be compatible with these so-called reinforcing or structural metals or materials, that is to say:
  a material which would adhere better, particularly to said structural material, so to obtain either non-slippery coating layers of bioreactive material on the structural material, or better quality reinforced composites which will not split.
  material with a coefficient of expansion very close to, and preferably no higher than that of said structural materials, particularly Ti, so as to avoid any crack formation.

They have sought to obtain a bioreactive material which is less reactive with bone tissue, so that the layer of reaction with the bone tissue is thin and yet has improved strength and can bear heavy mechanical loads; a further purpose being to reduce the propagation of the slow dissolution (demineralisation) reaction in the material, which tends to degrade the bioglass, thereby improving its resistance to fracture.

The object is to obtain biological anchoring which is still stronger and more homogeneous, so as to lengthen the life and increase the strength of the prosthesis and implant, and preferably to improve the anchoring with a secondary mechanical gripping effect, obtained by the growth of bone tissue into the rough parts or undulations which may form on the surface of the bioreactive material.

Applicants have also attempted to find methods of obtaining reinforced or plated composite pieces based on the bioreactive material and the reinforcing materials, since a method which helps to improve adhesion of the bioreactive material and structural material is preferable to the use of a molten glass technique. The method of impregnating a fibrous perform by dipping it into liquid glass, as described e.g. in U.S. Pat. No. 4,478,904 (DUCHEYNE), does not in fact apply to Ti, which would react with the glass at the high temperatures used.

DETAILED DESCRIPTION OF INVENTION

The invention is an improved bioreactive material of limited reactivity, generally used to obtain composite pieces with a structural material which has a low coefficient of expansion, for a bone prosthesis or dental implant, the bioreactive material being welded onto the bone tissue by chemical bonding, the chemical bond being free from any ossification defect and at the same time being thin and having much improved mechanical strength, the bioreactive material also having a low coefficient of expansion and very good adhesion to said structural material, characterised in that it contains, in percentages by weight, 5-14% of $Na_2O$, 0-12% of $P_2O_5$, 49-57% of $SiO_2$, the balance being no more than 33% of a mixture of CaO and $CaF_2$, the latter being from 0.5 to 7%.

But this material preferably contains 8-12% of $Na_2O$, 4-8% of $P_2O_5$, 50-54% of $SiO_2$, the balance still being no more than 33% and made up of CaO and $CaF_2$, the latter preferably being from 0.5 to 5%. The material is of the glass type, preferably partially crystallised glass; in some cases the glass may be totally crystallised. Thus such a material allows for particularly strong, resistant biological anchoring, by bonding or chemical welding to the bone tissue.

The reaction layer in said material, i.e. the layer which reacts with bone tissue, is very thin yet very strong. In addition the reaction forming the chemical bond is not propagated inside the bioreactive material; this avoids any deterioration of mechanical properties, particularly resistance to fracture. The material has been found to be less bioreactive than the known glasses described in the above-mentioned documents, but bioreactive enough to carry out biological anchoring; the bioreactive layer can withstand heavier loads or stronger forces. The structural materials with good bio-compatibility which are envisaged to obtain the composite pieces are generally infusible and inert relative to the bioreactive material, under the conditions for preparing the composites which will be described later. They are selected from metals such as Ti and its alloys, but also from Ta, Nb and their alloys, or from ceramics such as carbides, borides or nitrides, monocrystals such as corundum, sapphires, diamonds, etc. They may be used in the form of powder, dispersed long or short fibres (whiskers), fibrous preforms or other pieces in porous form (obtained e.g. by fritting powder), solid pieces which may be filled or hollow, or the like.

To obtain good adhesion between the bioreactive material and the structural material it is important for their coefficient of expansion to be similar, and preferably for that of the bioreactive material to be slighly lower than that of the structural material. This avoids dangers of cracking and embrittlement of the bioreactive material, particularly during the cooling phases which take place in the production process. Thus it will be noted that the structural materials have a low coefficient of expansion, always less than $10^{-5}K^{-1}$ at from 0° to 100° C., whereas a stainless steel has a high coefficient of expansion, close to $1.6.10^{-5}K^{-1}$.

Thus the bioreactive material according to the invention has a coefficient of expansion generally below $10^{-5} K^{-1}$ and adheres perfectly to the structural material, particularly to Ti (fibres, powder or the like) in solid or divided form.

The crystalline phases observed in the final product are chiefly devitrite $Na_2Ca_3Si_6O_{16}$ or $(Na_2O)(CaO)_3.(SiO_2)_6$, but also in a smaller quantity fluorapatite $Ca_{10}(PO_4)_6F_2$ and agrellite $NaCa_2Si_4O_{10}F$ or $(NaF((CaO)_2.(SiO_2)_4$. The presence of alumina and/or boron compounds is not desirable.

The precursor mix contains the above-mentioned elements in the required proportions. To obtain them the alkali metal oxide is introduced preferably in the form of at least one compound of the carbonate, phosphate, acid phosphate type or the like, the $P_2O_5$ preferably in the form of a phosphate or an alkali metal or alkali earth metal acid phosphate, such as $CaHPO_4$, $SiO_2$ is introduced as it is, and the alkaline earth metal oxide, generally CaO, is introduced preferably in the form of a carbonate, phosphate, oxide or fluoride, preferably in the form of $CaF_2$.

The powders are in proportions such that in the final product the contents of cations, phosphate and fluoride come within the ranges described above.

The powder mix is then melted, homogenised and cast, it is then cooled to obtain a non-crystallised glass. The glass can possibly be annealed, e.g. at 650° C. for 4 hours. The intermediate glass thus obtained is virtually free from crystalline phase and is then ground finely. The powder obtained has a homogeneous composition and is preferably used, in a second phase, to make the composites as will be seen later.

In this second phase the ground glass may equally be shaped by compressing or compacting cold then fritted naturally or under a load, or fritted directly under a load. Fritting under a load is always carried out after degassing by putting under vacuum; it is uniaxial, multiaxial or preferably isostatic (HIP-Hot Isostatic Pressing). A piece of bioreactive material is then obtained, in the form of a glass which may contain a crystallised phase as described above. It will be seen that this second phase of the process, following the obtaining of the ground intermediate glass and leading to the final bioreactive product, generally takes place without passing through the liquid state.

It is important that the intermediate glass, obtained after fusion of the initial powder then solidification, does not have any crystalline phase. In fact there may be serious difficulties in obtaining the desired crystallised phases in the final bioreactive material obtained after fritting, and particularly in the production (by the process described later) of high quality cladding materials or reinforced composites (particularly those made from a skeleton of porous structural material).

It is essential to keep the composition within the prescribed limits, given that the various constituent elements are imbricated, have effects on the structure of the final product and have an optimum reaction with the body fluid. With such a combination one can, surprisingly, obtain a set of properties which will greatly improve the biological anchoring, the mechanical properties of the final product, the adhesion to the structural materials required to obtain composite pieces, and improved biocompatibility and innocuousness.

Thus it will be noted that when the alkali metal oxide content of the final product, expressed as $Na_2O$, is too low, then apart from the melted mixture being insufficiently fluid and the difficulty of obtaining a glass, crystallisation in the final product is too rapid and is ill-controlled. When the content is below 5% a non-crystallised glass is no longer obtained when the mixture of initial powders has been melted then cooled. With the minimum value prescribed one can also start up the reaction of chemical bonding with the bone tissue. If on the other hand the upper limit described is exceeded, it is no longer possible to obtain a low enough coefficient of expansion, and there is excessive reactivity of the glass with the body fluids and hence an increase in the tendency of the material to disintegrate in time, and an unfavourable weakening of the mechanical properties of the interface.

Similarly silica helps to obtain reduced bioreactivity; if the silica content is above the limits described, bioreactivity becomes too low at the expense of the strength of the interfacial bond with the bone; biological anchoring no longer takes place, e.g. if the $SiO_2$ content reaches 60%. If the content is below the limit described, the coefficient of expansion becomes inappropriate and bioreactivity becomes excessive, giving a reaction layer which is thick and not strong enough.

As for the obligatory presence of fluoride, this is necessary to facilitate the initiation and control of crystallisation in the second phase of the process. It also reduces bioreactivity, limits migration of the bonding reaction and thus limits dissolution and the risks of the glass disintegrating at depth. The fluoride reduces the thickness of the reaction layer to the limit of detection and improves its homogeneity; it also gives the material very great long term stability in a biological medium; dissolution is negligible and there is no embrittlement.

If the prescribed fluoride content is exceeded the following is observed, taking into account the low $Na_2O$ content and high $SiO_2$ content used simultaneously:

a reduction in the fluidity of the molten glass, with a probability that it will no longer be obtained:

uncontrolled and harmful initiating of crystallisation in the intermediate glass;

poor control of crystallisation in the sintering treatments of the second phase of the process (said crystallisation should preferably take place slowly), leading to final products (particularly composites) of insufficient quality;

gradual suppression of the biological anchoring reaction.

It is preferable to limit the fluoride as far as possible, in order to reduce the risks of toxicity resulting from too large a quantity. As already stated, this limitation is obtained by using a combination of limited quantities of $Na_2O$ and rather large ones of $SiO_2$. This also makes it possible to limit the reactivity of the final product and to obtain a coefficient of expansion compatible with the composites to be produced.

Thus the bioreactive material according to the invention is distinguished from that described in U.S. Pat. No. 4,488,908 (DUCHEYNE), as it is adapted to obtain composites with a structural material which has a low coefficient of expansion.

It is also differentiated from the materials in U.S. Pat. No. 4,775,646 (HENCH) in respect of the combined contents of $Na_2O$, $SiO_2$ and fluoride. In HENCH the high content of $Na_2O$ and the content of $SiO_2$ favourable to obtaining good reactivity are compensated for by a high fluoride content, necessary to reduce reactivity adequately, while the coefficients of expansion obtained are high. With such compositions it thus appears difficult to obtain the low coefficients of expansion required in the invention, and to avoid the disadvantages due to the high fluoride content (toxicity, crystallisation, etc.).

Finally, this document does not suggest a product of a composition disclosed in the JMS document, in which CaO is substituted by $CaF_2$; in fact the minimum fluoride content which would thus be suggested would be above the highest limit described in the invention.

The material of the invention is particularly adapted to make composite bone prostheses or dental implants, that is to say, it is generally used in association with another, so-called structural material which serves to reinforce it. The structural material must be infusible and chemically inert under the conditions in which the composite is prepared. The composites may be of the reinforced or plated type.

In reinforced composite pieces the two materials—bioreactive and structural—are intimately bonded; the structural material may initially be either in the form of powders or dispersed fibres, in bulk, mixed with the powders of the bioreactive material, or in the form of a porous skeleton (which is a fritted or non-fritted preform, made up of tangled fibres, or a porous preform of fritted material) into which the bioreactive material will be introduced. The skeleton generally has a pore volume of from 15 to 90% and preferably 30 to 70% of the total volume, before it is covered with the bioreactive material.

In plated composite pieces a solid, either hollow or filled piece, made of structural material, is covered with a very adhesive layer of bioreactive material.

The bioreactive material according to the invention is particularly suitable for making composite pieces based on Ti; such a combination results in the quasi disappearance of the intermediate layer, which then measures only 0.02 to 2 microns, and in the complete disappearance of the bubbles of non-ossified tissue, which were noted with the use of prior art composites made of bioglass and stainless steel.

The invention also concerns the method of obtaining composite pieces containing structural material as described above. It includes the following stages:

a) mixing powders of alkali metal carbonate, silica, alkaline earth metal oxide, phosphate and fluoride, in the desired proportions.

b) melting the mixture and homogenising it, preferably in a closed receptacle so as to limit the liberation of fluoride.

c) casting to fractionate the charge and cooling it. At this stage a glass according to the invention is obtained, which may be treated by annealing as already mentioned.

d) finely grinding the glass obtained in Stage c), to obtain a non-crystalline powder of a mean particle size less than about 100 microns and preferably less than 40 microns, which may possibly be dried.

e) then proceeding to obtain the composite in the crude state, possibly after conditioning and/or suitably preparing the structural material. Several different embodiments may be applied according to the type of composite pieces required:

for a reinforced composite
either mixing the structural material, preferably mixing it dry, in the form of a powder or dispersed fibres, with the powder of ground, dried bioreactive material from Stage d), the mixture being placed in a mould to shape it.

or placing a porous skeleton or a solid piece covered with a porous skeleton of structural material in a mould, and spreading the ground, non-crystallised glass from Stage d) evenly in the mould around the skeleton or piece. It is not out of the question that, when the ground glass is spread around the porous pieces, it will not enter the pores, and this is an advantage.

for a plated composite, placing a solid piece of structural material in a mould and spreading the powder from Stage d) evenly in the mould around the piece.

f) Once the material has been moulded the following steps are taken:

for a reinforced composite without any porous skeleton:
either cold pressing followed by thermal treatment comprising natural sintering (or co-fritting) (solution 1) or sintering under a load (solution 2)
or sintering directly under a load (solution 3)

for a reinforced composite comprising a porous skeleton or comprising a solid piece covered by a porous skeleton: solution 2 and preferably solution 3.

for a plated composite: solution 1 or 2 and preferably solution 3.

Sintering under a load is carried out when the mould has been closed and degassed under vacuum; it may be uniaxial or multiaxial, but isostatic fritting (HIP) is preferable.

When sintering under a load pressure must be applied as soon as the glass is sufficiently fluid and before crystallisation reduces its fluidity. The operation generally takes place at from 500°-850° C., preferably from 600° to 800° C. at a temperature at least above the softening temperature of the glass and under high pressure, the pressure generally being from 50 to 1000 bars. These conditions are maintained for at least 1 minute and preferably at least 15 minutes but they must not be continued for over 5 hours and preferably not over 2 hours, in order to avoid a harmful enlargement of the crystals.

g) Cooling, preferably slowly, at least within the range from about 500° C. to ambient temperature.

h) Polishing or machining may be carried out to eliminate any peripheral defects such as surface cracks or the like, since the core of the piece is generally free from defects. For reinforced composite pieces with a porous skeleton of a structural material, particularly Ti, it is advantageous to continue machining until the structural material appears at the surface of the composite piece.

It should be noted that use of the HIP process is particularly favourable to obtaining good adhesion between the bioreactive material and the structural material, especially when it is a metal and particularly Ti.

Such a process generally gives a crystallisation rate for the bioreactive material of at least 40% and more generally over 80%; in some cases this rate may go up to total crystallisation.

The product then obtained is either a cosintered composite containing grains or fibres of structural material dispersed in the bioreactive material, or a plated composite where the core of structural material is covered with a layer of bioreactive material, or a composite where the structural material is in the form of a porous skeleton which may or may not cover a solid piece, its pore volume being totally filled by the bioreactive material.

In cases where the composite piece is a dental implant, the invention makes it possible to form a generally cylindrical implant comprising a solid core covered with a porous skeleton and containing a coaxial cavity in which a rod may be placed (with a view to fixing a permucosal passage there); in this way metallic continuity will be obtained between the skeleton and the core.

A process of this type is particularly recommended for making composites based on Ti, which cannot be put into contact with the molten bioreactive material without reacting. Either the glass powder and the mixed Ti fibres are cosintered, or the biomaterial is cosintered on the solid piece made of Ti, possibly with surface incrustations between the metal and the bioreactive material, or the biomaterial penetrates into the porous skeleton, as the case may be. The process also applies to the other structural materials already mentioned. But to the extent that the other materials do not react with the molten bioreactive material, the sintering process may be replaced by dipping the porous skeleton in the molten bath, then cooling it and possibly annealing it at about 750° C. for 4 hours.

It is often helpful though not necessary to prepare and/or condition the structural material, (e.g. the powder, fibres, porous skeletons, solid pieces, etc.) before putting it into contact with the powder which is a precursor of the biomaterial.

These treatments, which may comprise chemical pickling or other surface treatments, improve adhesion between the materials.

With the structural materials either showing or not showing at the surface of the composites according to the invention, one is free from the harmful inflammation during osteogenesis, which is observed at the bone-composite interface with the stainless steel/glass composites of prior art. Hence there is no disadvantage in baring the structural material and exposing it to body fluids at the periphery of a prosthesis, and the prosthesis can be machined without having any unacceptable result from the point of view of osteogenesis.

There is always excellent adhesion between the bioreactive material and the structural material.

EXAMPLES

Example 1 will illustrate the problems encountered in composite implants made in accordance with prior art; Example 2 will illustrate the making of composite implants according to the invention, and the results obtained after implantation in an animal.

EXAMPLE 1

Dental implants are made in accordance with prior art, using stainless steel and a type 45-S-5 glass containing (by weight):
$SiO_2$: 45%
$Na_2O$: 24.5%
$CaO$: 24.5%
$P_2O_5$: 6%

They are formed by a hollow cylindrical piece, closed at one end, the piece being a composite of stainless steel fibre impregnated with bioreactive glass 45-S-5, obtained by dipping the fibres in the molten glass. The piece is covered externally with a sheath of the bioreactive glass, except at the end which is left open. A solid piece made of stainless steel is fixed in the cavity in the cylindrical piece without any play. A stainless steel permucosal passage may be fixed to the upper end of the solid piece, to provide a link between the above unit, described as the root, and the buccal cavity, and to enable the dental prosthesis to be installed.

The presence of a sheath of bioreactive glass around the root is necessary, in order to avoid direct contact between the bone tissue and the stainless steel of the composite; this would prevent osteogensis, thus forming an unavoidable obstacle to good anchoring of the implant.

The implants are installed in the jaw of several dogs, from which some of the teeth are missing.

After 3 months of implantation half of them are resected and analysed microscopically and microchemically.

Cracks are observed in the glass sheath, bringing the stainless steel fibres into contact with the body fluids, and local inhibition of osteogenesis is observed, through the simultaneous action of the stainless steel ions and the glass ions; the cracks may themselves lead to inflammation.

The other half of the implants are subjected to masticatory forces after installation of the permucosal passage. Most of the implants are found to be defective under a load, due to the weakening of the bond between the bioreactive glass sheath and bone tissue. Embrittlement is also caused by the presence of an excessively thick reaction layer, of some hundreds of microns, at the outer surface of the glass sheath. Since the glass is too reactive, the chemical reaction is easily propagated within the sheath, and changes in the composition of the glass are noted, tending to embrittle it.

EXAMPLE 2

This describes the preparation of a composite dental implant according to the invention as an illustration of the invention, and the results after implantation in an animal.

A skeleton of Ti fibres is first made. Bulk fibres 4 mm long and about 50 microns in diameter are used for this purpose. The length and diameter are adjustable according to the size of the pieces to be produced. They may be much larger e.g. if bone prostheses of larger dimensions have to be made.

It is preferable for the fibres to undergo conditioning treatment, which in this case is as follows:
separating them on a large mesh vibrating screen;
pickling them with an aqueous solution containing 20% nitric acid and 2% hydrofluoric acid;
washing and drying them, then carrying out a second screening operation;
precompacting and loosening them.

The fibres are then compacted cold, directly to the desired final shape and dimension, allowing for the predictable shrinkage on sintering and for the filling of the pore volume, to obtain a porous cylindrical skeleton (cavity ratio 60%) and non-agglomerated fibres are removed. Fritting is carried out under vacuum under 1150° C. for 2 hours.

A hole is machined in the axis of the cylinder and a piece made of solid titanium is fitted therein (this installation is designed for subsequent mounting of a permucosal passage, which is necessary to position the dental prosthesis). After alkaline pickling, a second sintering operation is carried out, to bond the solid titanium to the fibrous skeleton.

Anodisation is then preferably carried out, to improve the adhesion of the of the bioreactive ceramic, using an electrolyte containing $H_3PO_4$—$H_2$-

SO₄—Na₂HPO₄—SiO₂. xH₂O. A powder mixture containing the following (by weight):
SiO₂: 41.0%
Na₂CO₃: 13.5%
CaCO₃: 33.9%
CaHPO₄: 9.1%
CaF₂: 2.5%
is prepared and placed in a covered crucible.

It is melted at 1350° C., homogenised and cast to fractionate the charge.

When it has cooled, the mixture is annealed at 650° C. for 4 hours and left to cool for 20 hours. It is ground to give a mean particle size of 15 microns. The powder is dried. The Ti skeleton is placed in a copper mould with the dried powder all round it, and the mould is closed under vacuum by welding. Isostatic sintering is carried out by bringing the temperature to 800° C. at a rate of 30° C. per minute, by applying at that point a pressure changing regularly from 200 to 1000 bars, and by maintaining these conditions for 1 hour. The material is left to cool slowly. After demoulding, the composite obtained is polished and put into its final form with the Ti fibres showing on the surface. The surface distribution of Ti is homogeneous, and the ratio of the area of visible fibres to the area of bioactive material is in the vicinity of 65.

The results obtained are as follows: the final content of F is 0.92% (by weight). As before, the implant is installed in that form in the jaw of some dogs.

The following is observed after 3 months of implantation:
- the interface between the titanium/bioreactive glass composite and the bone tissue does not show any defect of heterogeneity as previously; osteogenesis is not disturbed, although the metal fibres are exposed to body fluids.
- the reaction layer is homogeneous and has an extremely reduced thickness (a few microns); similarly the changes in the composition of the bioreactive material have very little depth and do not embrittle the glass. The osseous bond and the osteoconductive properties of the bioreactive material are maintained well. Thus the material remains intact and retains its strength.

Consequently no defects are noted in the mechanical action of the osseous bond, and no cracks or other defects in the glass and the implant.
- the osseus bond with the bioreactive material is already almost complete. The bone formed appears to go from one level of bioreactive material to another by forming a small bridge of bone tissue spanning the visible Ti fibres. In the intermediate zone between the Ti fibres and the osseous bridge one sometimes finds connective tissue, in contact with the Ti and covered with osteoid material. This intermediate zone will thus be converted into bone tissue, which will provide direct contact between the bone tissue and the titanium.

What is claimed is:

1. A method of preparing an improved bioreactive material for implantation into a human or animal body with chemical bonding to bone tissue, and consisting essentially of, by weight, 5-14% Na₂O, 0-12% P₂O₅, 49-57% SiO₂, and balance, no more than 33% CaO plus CaF₂, said material containing 0.5-7% CaF₂, comprising the steps of:

a) preparing a mixture of powders constituting a precursor of said bioreactive material, said mixture consisting essentially of silica, calcium fluoride, at least one sodium compound selected from the group consisting of oxide, carbonates, and phosphates, and at least one calcium compound selected from the group consisting of oxide, carbonates, and phosphates;

b) melting, homogenizing, casting and cooling said mixture to obtain an intermediate, non-crystallized glass;

c) grinding, degassing, and sintering said intermediate non-crystallized glass; and d) cooling said ground, sintered glass to obtain said bioreactive material.

2. The method according to claim 1, additionally comprising annealing said intermediate, non-crystallized glass before grinding.

3. The method according to claim 1, additionally comprising shaping by pressing said ground, non-crystallized glass before degassing.

4. The method according to claim 1, wherein said sintering is performed under pressure.

5. The method according to claim 1, 3 or 4, additionally comprising placing said ground, non-crystallized glass in contact with a second material to form a unit, followed by said steps of degassing, sintering and cooling, to thereby form a composite of said bioreactive material and said second material.

6. The method of claim 4 or 5, wherein the sintering comprises hot isostatic pressing (HIP).

7. The method according to claim 5, wherein said placing step comprises placing a solid structural member of said second material in a mold, and spreading said ground, non-crystallized glass evenly around said solid member, said composite being a plated composite.

8. The method according to claim 5, wherein said placing step comprises mixing, in a mold, said ground non-crystallized glass with a said second material, which comprises powder or dispersed fibers, said composite being a co-sintered composite.

9. The method according to claim 5, wherein said placing step comprises placing a porous skeleton comprising said second material, or a solid piece covered by a porous skeleton comprising said second material into a mold, and spreading said ground non-crystallized glass evenly therearound in said mold, the composite being a reinforced composite.

10. The method according to claim 9, wherein said porous skeleton comprises Ti fibers, and is formed from bulk Ti fibers by the successive steps of deagglomeration by screening, an initial pickling, annealing, cooling, a second screening, precompacting, deagglomerating, compacting cold into a desired shape, sintering under vacuum, and pickling with an alkaline solution.

11. The method of claim 10, wherein the initial pickling is with a nitric acid solution containing hydrofluoric acid.

12. The method according to claim 5, wherein said ground glass has a mean particle size less than 100 microns.

13. The method according to claim 12, wherein said mean particle size is less than 40 microns.

14. The method according to claim 5, wherein said step of sintering is carried out under a pressure of 50 to 1000 bars at a temperature of 500° C. to 850° C., which is above the softening point of the non-crystallized glass, for at least 1 minute and no longer than 5 hours.

15. The method according to claim 14, wherein the sintering is carried out for at least 15 minutes and no longer than 2 hours, at a temperature of 600°-800° C.

16. The method according to claim 5, additionally comprising polishing or machining the composite such that the structural material is visible at a surface of the composite.

* * * * *